United States Patent [19]
Mori et al.

[11] Patent Number: 6,156,930
[45] Date of Patent: Dec. 5, 2000

[54] METHOD FOR PRODUCING TRIFLUOROMETHANESULFONYL CHLORIDE

[75] Inventors: Kaoru Mori, Saitama; Takanori Hamana; Shigenori Sakai, both of Yamaguchi; Tadayuki Kawashima, Saitama, all of Japan

[73] Assignee: Central Glass Company, Limited, Ube, Japan

[21] Appl. No.: 09/472,885

[22] Filed: Dec. 28, 1999

[30] Foreign Application Priority Data

Dec. 28, 1998 [JP] Japan ................................. 10-374008
Dec. 28, 1998 [JP] Japan ................................. 10-374009
Mar. 16, 1999 [JP] Japan ................................. 11-070601

[51] Int. Cl.$^7$ .................................................. C07C 309/06
[52] U.S. Cl. ......................................... 562/829; 562/834
[58] Field of Search ..................................... 562/829, 834

[56] References Cited

U.S. PATENT DOCUMENTS 2,732,398   6/1956   Brice et al. ............................. 260/503

FOREIGN PATENT DOCUMENTS 54344   2/1991   Hungary .

*Primary Examiner*—Mukund J. Shah
*Assistant Examiner*—Hong Liu
*Attorney, Agent, or Firm*—Evenson, McKeown, Edwards & Lenahan, P.L.L.C.

[57] ABSTRACT

The present invention provides a method for producing trifluoromethanesulfonyl chloride. This method includes the step of reacting trifluoromethanesulfonic acid with phosphorous trichloride and chlorine. With this method, trifluoromethanesulfonyl chloride can be easily and highly selectively produced at high yield. The reaction may be carried out at about atmospheric pressure. Furthermore, the reaction may be carried out in the presence of phosphorus oxychloride either under a pressurized condition or at about atmospheric pressure.

18 Claims, No Drawings

METHOD FOR PRODUCING TRIFLUOROMETHANESULFONYL CHLORIDE

BACKGROUND OF THE INVENTION

The present invention relates to a method for producing trifluoromethanesulfonyl chloride. Trifluoromethanesulfonyl chloride is a useful compound that is used as a raw material during production of, for example, pharmaceuticals, agricultural chemicals and various types of functional materials.

Chemical Abstracts 115:50301 discloses that trifluoromethanesulfonyl chloride is obtained by reacting trifluoromethanesulfonic acid with phosphorus trichloride.

As is shown in the reaction formula below, U.S. Pat. No. 2,732,398 discloses a process of producing trifluoromethanesulfonyl chloride, in which trifluoromethanesulfonic acid is reacted with phosphorous pentachloride.

$$CF_3SO_3H+PCl_5 \rightarrow CF_3SO_2Cl+POCl_3+HCl$$

In this production process, however, since the phosphorous pentachloride used as raw material is a solid, there may be problems with the manner of its addition. Namely, the workability when adding phosphorous pentachloride may be poor, thus making this process unsuitable for industrial production of trifluoromethanesulfonyl chloride.

SUMMARY OF THE INVENTION

It is an object of the present invention to provide a method for producing trifluoromethanesulfonyl chloride efficiently with an improved workability.

According to the present invention, there is provided a method for producing trifluoromethanesulfonyl chloride. This method comprises reacting trifluoromethanesulfonic acid with phosphorous trichloride and chlorine.

According to a first aspect of the present invention, the reacting is carried out at about atmospheric pressure.

According to a second aspect of the present invention, the reacting is carried out in the presence of phosphorus oxychloride. In fact, this reacting may be carried out under a pressurized condition or at about atmospheric pressure.

DESCRIPTION OF THE PREFERRED EMBODIMENTS

It was unexpectedly found that trifluoromethanesulfonyl chloride ($CF_3SO_2Cl$) can be easily and highly selectively produced at high yield by reacting trifluoromethanesulfonic acid ($CF_3SO_3H$) with phosphorous trichloride ($PCl_3$) and chlorine ($Cl_2$), as shown by the following reaction formula.

$$CF_3SO_3H+PCl_3+Cl_2 \rightarrow CF_3SO_2Cl+POCl_3+HCl$$

In the present invention, the molar ratio of phosphorous trichloride to chlorine is preferably in the vicinity of 1:1.

The amount of each of phosphorous trichloride and chlorine, which are used in the present invention, is preferably no more than 2 moles, and more preferably 0.5 to 2.0 moles, to 1 mole of trifluoromethanesulfonic acid. If the molar ratio of phosphorous trichloride to trifluoromethanesulfonic acid is too high, a large amount of the raw material of phosphorous trichloride remains, which may be undesirable since it may place a burden on the following purification process. The yield of target product (trifluoromethanesulfonyl chloride) may not increase significantly even if the molar ratio of phosphorous trichloride or chlorine to trifluoromethanesulfonic acid exceeds 2.0. Therefore, the molar ratio of phosphorous trichloride or chlorine to trifluoromethanesulfonic acid is preferably no more than 2.0 in order to carry out the reaction efficiently. In addition, if the molar ratio of phosphorous trichloride or chlorine to trifluoromethanesulfonic acid is too low, the amount of by-product in the form of trifluoromethanesulfonic anhydride [$(CF_3SO_2)_2O$] increases, which may be undesirable since it may cause a decrease in the yield of trifluoromethanesulfonyl chloride. The yield of trifluoromethanesulfonyl chloride may fall to 50% or less if the molar ratio of phosphorous trichloride or chlorine to trifluoromethanesulfonic acid is less than 0.5. Therefore, the molar ratio of phosphorous trichloride or chlorine to trifluoromethanesulfonic acid is preferably no less than 0.5 in order to carry out the reaction efficiently. It is more preferable that the amount of each of phosphorous trichloride and chlorine be 0.8 to 1.2 moles to 1 mole of trifluoromethanesulfonic acid to carry out the reaction more efficiently.

In the present invention, a reactor is charged with trifluoromethanesulfonic acid, phosphorous trichloride and optionally phosphorus oxychloride, and then chlorine is introduced into the reactor, in order to conduct the reaction. Since heat is generated when chlorine is introduced, the temperature during this introduction is preferably not higher than 50° C., and more preferably 10–30° C. In fact, according to the second aspect of the present invention, a reactor is charged with trifluoromethanesulfonic acid, phosphorous trichloride and phosphorus oxychloride, and then chlorine is introduced into the reactor. After that, the reaction is conducted at about atmospheric pressure or under a pressurized condition having a pressure, for example, of not higher than 10 kg/cm². In case that chlorine is introduced without the addition of phosphorus oxychloride, trifluoromethanesulfonic acid may be reacted with phosphorus trichloride during the introduction of chlorine such that an intermediate deposits in the form of crystals. This intermediate can be dissolved by adding phosphorus oxychloride into the reaction system. With this, it becomes possible to sufficiently stir the reaction mixture and to avoid clogging of a chlorine introduction tube. According to the second aspect of the present invention, phosphorus oxychloride is in an amount by volume of preferably up to three times, more preferably from 0.2 to 3.0 times, still more preferably from 0.8 to 2.0 times, that of trifluoromethanesulfonic acid. If the amount of phosphorus oxychloride is too much relative to that of trifluoromethanesulfonic acid, it is possible to sufficiently stir the reaction mixture and to smoothly introduce chlorine into the reactor. However, the content of trifluoromethanesulfonyl chloride in the reaction product may become too low.

It is preferable that the reaction temperature be 40–100° C. Furthermore, a reaction temperature of 60–90° C. is more preferable, in order to allow the reaction to proceed more efficiently. The following optional condition is applied, for allowing the reaction to proceed more efficiently. In fact, it may be conducted under reflux condition. When it is conducted in batch process, it is preferable to continue the reaction for about 1–2 hours even after the increase of the inside pressure of the reactor has stopped. With this, it is possible to obtain trifluoromethanesulfonyl chloride highly selectively and at high yield.

In the present invention, as shown in the above reaction formula, the reaction product contains phosphorus oxychloride besides trifluoromethanesulfonyl chloride. The reaction product may further contain trifluoromethanesulfonic anhydride produced as by-product and the unreacted trifluoromethanesulfonic acid. Furthermore, according to the second aspect of the present invention, the reaction product contains phosphorus oxychloride that has been introduced into the reactor prior to the reaction. After the reaction, it is possible to easily separate target product (trifluoromethanesulfonyl chloride) from all of these substances to purify the reaction product. Thus, since trifluoromethanesulfonyl chloride can be obtained extremely easily and efficiently in the present invention, it offers the advantage of extremely good workability and productivity in comparison with the production process of the prior art.

The following nonlimiting examples are illustrative of the present invention. In fact, Example 1 is illustrative of the first aspect of the present invention, and Examples 2–6 are illustrative of the second aspect of the present invention.

EXAMPLE 1

At first, a 300-ml, three-necked, glass flask was charged with 150.0 g (1.0 mole) of trifluoromethanesulfonic acid and then with 137.2 g (1.0 mole) of phosphorous trichloride. Next, 50.0 g (0.7 moles) of chlorine were introduced at 20–40° C. After introducing the chlorine, the reaction mixture was heated to 70° C. and refluxed for 4 hours. Following completion of the reaction, the reaction mixture was distilled to obtain 102.3 g of trifluoromethanesulfonyl chloride (yield: 60.7%) as a distillate having a boiling point of 25–40° C. In addition, after distilling off trifluoromethanesulfonyl chloride, the mixture was distilled under reduced pressure to obtain 16.2 g of trifluoromethanesulfonic anhydride (yield: 11.3%) as a distillate having a boiling point of 45–50° C. at a pressure of 150 mmHg.

EXAMPLE 2

At first, a 500-ml, pressure-tight, glass reactor was charged with 150.0 g (1.0 mole) of trifluoromethanesulfonic acid and then with 137.3 g (1.0 mole) of phosphorus trichloride.

Under cooling with ice, 306.7 g (2.0 moles) of phosphorus oxychloride were added to the reactor. Then, 70.9 g (1.0 mole) of chlorine were introduced at 7–14° C. After introducing the chlorine, chlorine introduction and exhaust valves were closed.

After that, the reaction mixture was heated to 80° C. 2 hr after this heating, the inside pressure of the reactor reached 2.8 kg/cm² (absolute pressure). The reaction was conducted for 4 hr at 80° C., followed by cooling. When the reaction liquid was cooled down to 10° C., stirring was stopped. Then, hydrogen chloride was purged from the reactor. Then, the reaction liquid was distilled to obtain 101.4 g (yield: 60.2%) of trifluoromethanesulfonyl chloride as a distillate having a boiling point of 25–35° C.

EXAMPLE 3

At first, a 500-ml, pressure-tight, glass reactor was charged with 105.0 g (0.7 moles) of trifluoromethanesulfonic acid and then with 96.1 g (0.7 moles) of phosphorus trichloride. Under cooling with ice, 161.0 g (1.05 moles) of phosphorus oxychloride were added to the reactor. Then, 49.7 g (0.7 moles) of chlorine were introduced at 13–20° C. After introducing the chlorine, chlorine introduction and exhaust valves were closed. After that, the reaction mixture was heated to 80° C. 2 hr after this heating, the inside pressure of the reactor reached 2.5 kg/cm² (absolute pressure). The reaction was conducted for 4 hr at 80° C., followed by cooling. When the reaction liquid was cooled down to 15° C., stirring was stopped. Then, hydrogen chloride was purged from the reactor. Then, the reaction liquid was distilled to obtain 77.9 g (yield: 66.1%) of trifluoromethanesulfonyl chloride as a distillate having a boiling point of 25–31° C.

EXAMPLE 4

At first, a 1-liter, four-necked, glass flask was charged with 200.5 g (1.3 moles) of trifluoromethanesulfonic acid and then with 221.3 g (1.6 moles) of phosphorus trichloride. Then, under cooling with water, 148.7 g (0.97 moles) of phosphorus oxychloride were added to the reactor. Then, 70.0 g (1.0 mole) of chlorine were introduced at 20–45° C. After introducing the chlorine, the reaction mixture was heated to 70° C. and refluxed for 4 hours. Following completion of the reaction, the reaction mixture was distilled to obtain 87.5 g of trifluoromethanesulfonyl chloride (yield: 38.9%) as a distillate having a boiling point of 25–35° C. In addition, after distilling off trifluoromethanesulfonyl chloride, the mixture was distilled under reduced pressure to obtain 58.6 g of trifluoromethanesulfonic anhydride (yield: 31.1%) as a distillate having a boiling point of 42–50° C. at a pressure of 140–150 mmHg.

EXAMPLE 5

At first, a 1-liter, four-necked, glass flask was charged with 200.0 g (1.3 moles) of trifluoromethanesulfonic acid and then with 183.5 g (1.3 moles) of phosphorus trichloride. Then, under cooling with water, 202.9 g (1.3 moles) of phosphorus oxychloride were added to the reactor. Then, 95.0 g (1.3 mole) of chlorine were introduced at 22–32° C. After introducing the chlorine, the reaction mixture was heated to 75° C. and refluxed for 4 hours. Following completion of the reaction, the reaction mixture was distilled to obtain 201.1 g of trifluoromethanesulfonyl chloride (yield: 89.6%) as a distillate having a boiling point of 25–38° C. In addition, after distilling off trifluoromethanesulfonyl chloride, the mixture was distilled under reduced pressure to obtain 11.5 g of trifluoromethanesulfonic anhydride (yield: 6.1%) as a distillate having a boiling point of 45–50° C. at a pressure of 150 mmHg.

EXAMPLE 6

At first, a 1-liter, four-necked, glass flask was charged with 150.3 g (1.0 mole) of trifluoromethanesulfonic acid and then with 137.8 g (1.0 mole) of phosphorus trichloride. Then, under cooling with water, 298.8 g (1.9 moles) of phosphorus oxychloride were added to the reactor. Then, 80.0 g (1.1 moles) of chlorine were introduced at 20–31° C. After introducing the chlorine, the reaction mixture was heated to 81° C. and refluxed for 4 hours. Following completion of the reaction, the reaction mixture was distilled to obtain 151.2 g of trifluoromethanesulfonyl chloride (yield: 89.7%) as a distillate having a boiling point of 25–35° C. In addition, after distilling off trifluoromethanesulfonyl chloride, the mixture was distilled under reduced pressure to obtain 9.3 g of trifluoromethanesulfonic anhydride (yield: 6.6%) as a distillate having a boiling point of 42–50° C. at a pressure of 145 mmHg.

The entire disclosure of each of Japanese Patent Application Nos. 10-374008 filed on Dec. 28, 1998, 10-374009 filed on Dec. 28, 1998, and 11-070601 filed on Mar. 16, 1999, including specification, claims, and summary, is incorporated herein by reference in its entirety.

What is claimed is:

1. A method for producing trifluoromethanesulfonyl chloride, comprising reacting trifluoromethanesulfonic acid with phosphorous trichloride and chlorine.

2. A method according to claim 1, wherein said reacting is conducted at about atmospheric pressure.

3. A method according to claim 1, wherein each of said phosphorous trichloride and said chlorine is in an amount of 0.5–2.0 moles, relative to 1 mole of said trifluoromethanesulfonic acid.

4. A method according to claim 1, wherein each of said phosphorous trichloride and said chlorine is in an amount of 0.8 to 1.2 moles, relative to 1 mole of said trifluoromethanesulfonic acid.

5. A method according to claim 1, wherein a molar ratio of said phosphorus trichloride to said chlorine is about 1:1.

6. A method according to claim 1, wherein said reacting is conducted by (a) adding said phosphorus trichloride to said trifluoromethanesulfonic acid to obtain a mixture, and (b) introducing said chlorine into said mixture to conduct said reacting.

7. A method according to claim 6, wherein said introducing is conducted at a temperature of not higher than 50° C.

8. A method according to claim 1, wherein said reacting is conducted at a temperature of from 40 to 100° C.

9. A method according to claim 1, wherein said reacting is conducted under reflux.

10. A method according to claim 1, wherein said reacting is conducted in the presence of phosphorus oxychloride.

11. A method according to claim 10, wherein said reacting is conducted under a pressurized condition.

12. A method according to claim 11, wherein said pressurized condition has a pressure of not higher than 10 $kg/cm^2$.

13. A method according to claim 10, wherein said reacting is conducted at about atmospheric pressure.

14. A method according to claim 10, wherein said phosphorus oxychloride is in an amount by volume of from 0.2 to 3.0 times that of said trifluoromethanesulfonic acid.

15. A method according to claim 10, wherein said phosphorus oxychloride is in an amount by volume of from 0.8 to 2.0 times that of said trifluoromethanesulfonic acid.

16. A method according to claim 10, wherein said reacting is conducted by (a) mixing together said trifluoromethanesulfonic acid, said phosphorus trichloride, and said phosphorus oxychloride to obtain a mixture, and (b) introducing said chlorine into said mixture to conduct said reacting.

17. A method according to claim 16, wherein said introducing is conducted at a temperature of not higher than 50° C.

18. A method according to claim 1, wherein said reacting is conducted at a temperature of from 40 to 100° C.

* * * * *

UNITED STATES PATENT AND TRADEMARK OFFICE
CERTIFICATE OF CORRECTION

PATENT NO.    : 6,156,930
DATED         : December 5, 2000
INVENTOR(S)   : Kaoru Mori Page 1 of 1

It is certified that error appears in the above-identified patent and that said Letters Patent is hereby corrected as shown below:

<u>Column 4,</u>
Line 65, insert -- liquid -- before "phosphorous trichloride".

Signed and Sealed this

Ninth Day of July, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.    : 6,156,930
DATED         : December 5, 2000
INVENTOR(S)   : Kaoru Mori It is certified that error appears in the above-identified patent and that said Letters Patent is hereby corrected as shown below:

<u>Column 4,</u>
Line 67, insert -- liquid -- before "phosphorous trichloride".

This certificate supersedes Certificate of Correction issued July 9, 2002.

Signed and Sealed this

First Day of April, 2003

JAMES E. ROGAN
*Director of the United States Patent and Trademark Office*